(12) United States Patent
Voss

(10) Patent No.: US 7,028,564 B2
(45) Date of Patent: Apr. 18, 2006

(54) LOW FLOW BAILER SYSTEM

(76) Inventor: Gene A. Voss, P.O. Box 33238, San Antonio, TX (US) 78265

( * ) Notice: Subject to any disclaimer, the term of this patent is extended or adjusted under 35 U.S.C. 154(b) by 26 days.

(21) Appl. No.: 10/737,188

(22) Filed: Dec. 16, 2003

(65) Prior Publication Data
US 2005/0126313 A1 Jun. 16, 2005

(51) Int. Cl.
G01N 1/12 (2006.01)
E21B 27/00 (2006.01)

(52) U.S. Cl. ............................. 73/864.63; 73/863.72; 166/168

(58) Field of Classification Search ............ 73/864.63, 73/864.65, 864.66, 864.67, 863.72; 166/264, 166/162, 165, 167, 168
See application file for complete search history.

(56) References Cited

U.S. PATENT DOCUMENTS

| 4,928,541 | A | * | 5/1990 | Toon et al. | 73/864.63 |
| 5,404,949 | A | * | 4/1995 | Voss | 166/264 |
| 5,753,831 | A | * | 5/1998 | Mohs | 73/864.63 |
| 5,878,813 | A | * | 3/1999 | Ridgeway, Jr. | 166/162 |
| 6,543,302 | B1 | * | 4/2003 | Pratt | 73/864.63 |
| 2002/0104648 | A1 | * | 8/2002 | Pratt | 166/165 |

* cited by examiner

Primary Examiner—Charles Garber
(74) Attorney, Agent, or Firm—Naman, Howell, Smith & Lee

(57) ABSTRACT

An improved bailer which allows for the variance of flow into the bailer through use of attachments with varying inflow orifice sizes. As the size of the orifice changes, the weight of the apparatus can also be changed allowing for an only slightly negative buoyancy of the apparatus. The attachment may also be designed to include features for filtering unwanted particulates from the sample.

15 Claims, 1 Drawing Sheet

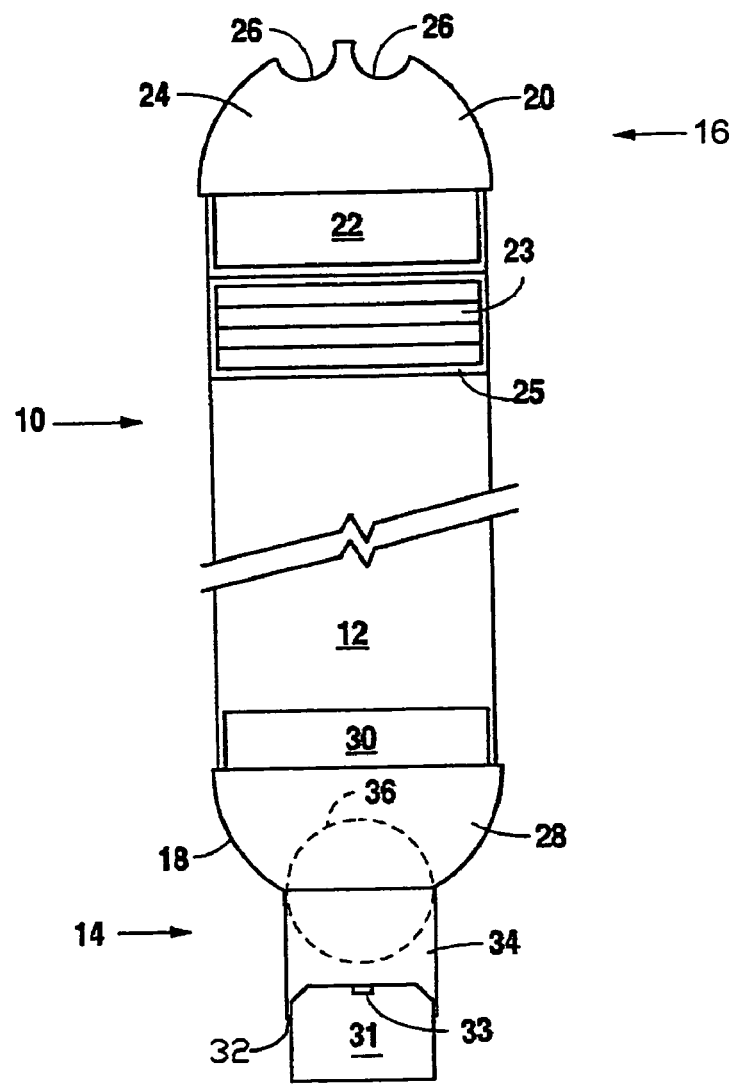
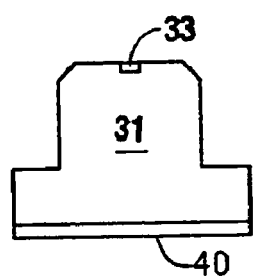
Fig. 1
Fig. 2

LOW FLOW BAILER SYSTEM

BACKGROUND OF THE INVENTION

1. Field of the Invention

Applicant's invention relates to apparatuses for retrieving liquid samples from reservoirs of liquid.

2. Background Information

Groundwater pollution is an ever-growing concern in today's environments, and the need for groundwater monitoring is increasing, especially around chemical storage facilities, land fills, military bases, airports, and underground storage tanks.

The typical groundwater monitoring program consists of a series of monitoring wells located at different points around the margin of an aquifer, in close and distant proximities from the potential contamination source. Each monitoring well consists of a well casing which lines the well bore, the hole extending from the ground surface to the groundwater.

At least until very recently, most monitoring samples have been taken through the use of devices known as bailers. A bailer is an elongated, slender tube which is sized to pass through the well casing of a test well. The insertion end of an advanced bailer includes a one-way valve which allows water to flow into the bailer as it is lowered into the well casing, but hinders effluent flow as the bailer is lifted from the water.

Bailers have been in widespread use in the groundwater sampling process because they are inexpensive to purchase, inexpensive to fabricate, portable, simple to operate, and require no external power source. However, inherent in the presently-known bailer designs, is the inability to control the flow rate of the sample—a serious problem in light of relatively new knowledge concerning factors affecting the quality of samples taken in test wells.

It has been determined that if the extraction rate exceeds the recharge rate, the sample may be compromised through various means, including the increase of the turbidity of the sample, the mixing of stagnant and fresh water in the well, and the disturbance and re-suspension of settled solids. The results of the sample analysis then may be skewed, showing either higher or lower levels of contamination in the groundwater then actually exist, depending on the characteristics of the contaminant. As a result, Federal and state governments now require that samples of ground water be extracted at a rate not exceeding the recharge rate of the sampling well. Resulting guidance documents now state that bailers are ill-suited for low flow. Thus, use of conventional bailers for test well sampling is very nearly obsolete.

The preferred method for test well sampling now involves the use of pumps. Ironically, although the pump flow rates are easily controlled, the problems associated with using pumps at test well sites are the very reasons that most samplers changed from using pumps to using bailers in the past. Pumps are expensive, harder to clean and operate, and require an external power source. Pumps also have go through general maintenance procedures to maintain the life of the pumps, increasing the cost.

In view of the foregoing, it would well serve those involved in test well monitoring to provide some means by which test well sample may be taken with the simplicity and economy of bailers, yet still comply with the new low-flow sampling requirements.

SUMMARY OF THE INVENTION

It is an object of the present invention to provide an improved bailer to allow for low flow sampling as is desirable to obtain quality samples from ground water test wells and, in some cases, required by the governmental regulations, in any event to provide an alternative to presently available, and much more expensive alternatives for obtaining such samples.

In satisfaction of these and related objectives, Applicant's present invention provides a bailer of an improved design which allows for the variance of flow into the bailer through use of attachments with varying inflow orifice sizes. As the size of the orifice changes, the weight of the apparatus can also be changed allowing for an only slightly negative buoyancy of the apparatus. The attachment may also be designed to include features for filtering unwanted particulates from the sample.

BRIEF DESCRIPTION OF THE DRAWINGS

FIG. 1 is an elevational side view of the Applicant's improved bailer with low-flow attachment engaged.

FIG. 2 is an elevations side view of the Applicant's low-flow attachment incorporating the filtering device.

DETAILED DESCRIPTION OF THE PREFERRED EMBODIMENT

Referring to FIG. 1, the bailer of Applicant's invention is identified by the reference numeral 10. The preferred embodiment of bailer 10 includes a cylindrical, plastic tube 12.

The bailer has an insertion or distal end 14 and a proximal end 16. The preferred embodiment of Applicant's bailer 10 includes a distal terminus cap 18 and a proximal terminus cap 20, and a negative buoyancy device 23 and housing 24. Proximal terminus cap 20 includes a generally dome-shaped portion 24 from which extends a nesting lip 22.

Nesting lip 22 extends from the margin of the dome portion 24 of cap 20 to generally define a cylindrical structure which snugly nests within the lumen of plastic tube 12. To insure that proximal terminus cap 20 does not accidentally disengage from plastic tube 12, the two should be suitably bonded together (such as through use of sonic welding) during assembly of bailer 10 through means appropriate for the material from which bailer 10 is fabricated (polyethylene in the case of Applicant's current preferred embodiment).

The preferred embodiment of proximal terminus cap 20 has two attachment orifices 26 passing through the dome-shaped portion 24. Attachment orifices 26 provide the means by which bailer 10 is attached to cording (not shown in the drawings) by which bailer 10 will be lowered into and removed from a well.

A terminal segment of cording will be passed through a first orifice 26 from the convex side of dome-shaped portion 24, and then passed through the other orifice 26 from the concave side of dome-shaped portion 24. In order to insure that bailer 10 assumes as near a vertical orientation as possible as it is suspended from a cord during sample taking, orifices 26 should reside as mirror images of each other on either side of a bisecting line which divides equally the dome-shaped portion 24 of terminus cap 20. For the same reason, the axis of symmetry of dome-shaped portion 24 should, when terminus cap 20 is installed on plastic tube 12, correspond to the longitudinal axis of symmetry of plastic tube 12.

The configuration of proximal terminus cap 20 as just described virtually eliminates the possibility of a bailer 10 becoming lodged against some irregularity in the well casing surface. Unlike the angular margins of presently available bailers, the purely rounded surfaces of Applicant's bailer 10 will simply slide past all obstructions in the well casing, except those which would have prevented initial insertion of bailer 10 in the first place.

The preferred embodiment of the negative buoyancy device 23 is a series of masses, in which the weight of the apparatus can be changed by removing or adding mass. The weight of the apparatus is used to aid in the control of the flow rate into the apparatus. The negative buoyancy device is enclosed in housing 25, which keeps the weights separate from the sample, thereby avoiding contamination. The preferred embodiment of the housing 25 is a cylindrical casing that should be permanently bonded to the bailer and is made of an inert material, to avoid contamination.

Distal terminus cap 18 also includes a generally dome-shaped portion 28 from which extends a nesting lip 30. Nesting lip 30 is configured substantially identically to nesting lip 22 of proximal terminus cap 20 and is attached in the same manner.

The preferred embodiment of distal terminus cap 18 exhibits an intake orifice 32, a flow control insert 31, and a flow control orifice 33, through which water passes when gathering a test sample. The orifice 32 is, in the preferred embodiment surrounded by an annular flange 34 which serve to prevent interference with operation of the ball valve 36 by objects which may contact the distal end 14 of bailer 10. The flow control insert 31, in the preferred embodiment is compression fit to the intake orifice 32 to shut off flow around the insert and direct the flow through the flow control orifice 33. The flow control orifice 33, in the preferred embodiment is centered on the inserted end of the flow control insert. The flow control orifice size varies and combined with the amount of weight in the negative buoyancy device 23 can control the fill rate of the apparatus ranging from less than 100 milliliters per minute to over 1 liter per minute.

The flow control insert 31 may also be covered with a particulate filtering device 40 as shown in FIG. 2. The filtering device 40 covers the in-take end of the flow control insert 31. It is used to prevent clogs occurring in the flow control orifice. The preferred embodiment of the filtering device is a stainless steel mesh screen that is placed over the protruding end of the flow control insert.

As with proximal terminus cap 20, distal terminus cap 18 is configured whereby the axis of symmetry of dome-shaped portion 28 should, when terminus cap 18 is installed on plastic tube 12, correspond to the longitudinal axis of symmetry of plastic tube 12. The orifice 32 is, in turn, centered on the same axis of symmetry of plastic tube 12. This configuration insures that orifice 32 (and flange 34) is directed parallel with the path of bailer 10 and is less likely to scrap sediment, etc. from the casing wall as the bailer 10 is lowered for sample gathering, and thereby risk contamination of the sample.

While the greater concern which is addressed by the rounding of margins for bailer 10 is that of avoiding juxtaposition of a proximal, angular margin with a casing surface irregularity after the bailer is inserted into a well casing, the rounding of the distal end 14 surfaces of bailer 10 also has significant utility.

Certain irregularities in well casings are not so profound as to risk trapping the bailer 10 in the well casing. Nevertheless, some irregularities may be pronounced enough such that an angular margin on the distal end of a bailer will abut the irregularity and thereby suspend the bailer above the level intended for sample taking.

Additionally, the engagement of a sharp edge with a well casing wall as the bailer is lowered may dislodge sediments and other accumulations on the well casing surface which may lead to local contamination of the underlying water supply to an extent which may render the sample unrepresentative of the actual over-all state of the water supply. In certain cases, this could lead to a "false positive" for serious levels of contaminants in a water supply, with potentially very costly and disquieting results. If, for example, a well test revealed an abnormal level of, perhaps, a heavy metal which had accumulated on the casing wall over time, but which was not at dangerous levels in the actual water supply, environmental regulations might, in the case of a producing water well, dictate suspension of operation of the subject well, and in other cases lead to costly investigations of nearby candidates for sources of pollution.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. An improved liquid sampling device comprising:
    an elongate, substantially cylindrical conduit member having first and second conduit ends;
    a first conduit member terminus;
    a second conduit member terminus, said second conduit member terminus being shaped to generally define a second convex dome extending outwardly from said conduit member at said second conduit end, said second convex dome portion of said second conduit member terminus being substantially centered on the longitudinal axis of symmetry of said conduit member, said second conduit member terminus having an in-take orifice defined therethrough and a valve member for valving passage of fluid through said in-take orifice; and
    a flow control insert having a flow control orifice and being sized and shaped for snug, nested engagement with said in-take orifice such that all flow continuously enters or exits said device exclusively via said flow control orifice, said flow control orifice having a cumulatively lesser cross section than said intake orifice.

2. The apparatus of claim 1 wherein said first conduit member terminus is shaped to generally define a first convex dome extending outwardly from said conduit member at said first conduit end, said first convex dome portion of said first conduit member terminus being substantially centered on the longitudinal axis of symmetry of said conduit member, said convex dome portion having cord attachment means.

3. The apparatus of claim 2 wherein said cord attachment means is comprised of first and second attachment orifices defined through said dome portion of said first conduit member terminus and separated by a portion of said dome portion of said first conduit member terminus, whereby a terminal end of an elongate cording member may pass into said apparatus through said first attachment orifice and exit said apparatus through said second attachment orifice whereafter said terminal end of said cording member may be secured to a medial portion of said cording member to secure an attachment between said cording member and said apparatus.

4. The apparatus of claim 3 further comprising negative buoyancy means for adjusting buoyancy of said apparatus when submersed in liquid.

5. The apparatus of claim 1 wherein said first conduit member terminus is a removable cap-like member having a first nesting lip extending from the circumferential margin of said first convex dome, said first nesting lip being configured for reversibly, slidably and snugly nesting within said conduit member at said first conduit end for reversibly attaching said first conduit member terminus to said conduit member.

6. The apparatus of claim 1 wherein said second conduit member terminus is a removable cap-like member having a second nesting lip extending from the circumferential margin of said second convex dome, said second nesting lip being configured for reversibly, slidably and snugly nesting within said conduit member at said second conduit end for reversibly attaching said second conduit member terminus to said conduit member.

7. The apparatus of claim 1 wherein said in-take orifice is defined by said second convex dome whereby said in-take orifice is centered on an axis of symmetry of said second convex dome.

8. The apparatus of claim 1, wherein said flow control insert further comprises means for filtering particulates.

9. The apparatus of claim 8 further comprising negative buoyancy means for adjusting buoyancy of said apparatus when submersed in liquid.

10. The apparatus of claim 2 wherein said first conduit member terminus is a removable cap-like member having a first nesting lip extending from the circumferential margin of said first convex dome, said first nesting lip being configured for reversibly, slidably and snugly nesting within said conduit member at said first conduit end for reversibly attaching said first conduit member terminus to said conduit member.

11. The apparatus of claim 2 wherein said second conduit member terminus is a removable cap-like member having a second nesting lip extending from the circumferential margin of said second convex dome, said second nesting lip being configured for reversibly, slidably and snugly nesting within said conduit member at said second conduit end for reversibly attaching said second conduit member terminus to said conduit member.

12. The apparatus of claim 2 wherein said in-take orifice is defined by said second convex dome whereby said in-take orifice is centered on an axis of symmetry of said second convex dome.

13. The apparatus of claim 2, wherein said flow control insert further comprises means for filtering particulates.

14. The apparatus of claim 13 further comprising negative buoyancy means for adjusting buoyancy of said apparatus when submersed in liquid.

15. The apparatus of claim 2 further comprising negative buoyancy means for adjusting buoyancy of said apparatus when submersed in liquid.

* * * * *